(12) United States Patent
Ozeki et al.

(10) Patent No.: US 8,852,656 B2
(45) Date of Patent: Oct. 7, 2014

(54) SLEEP IMPROVEMENT COMPOSITION

(75) Inventors: Makoto Ozeki, Yokkaichi (JP); Haruo Yao, Yokkaichi (JP); Tsutomu Okubo, Yokkaichi (JP); Lekh Raj Juneja, Yokkaichi (JP)

(73) Assignee: Taiyokagaku Co., Ltd., Yokkaichi-Shi (JP)

( * ) Notice: Subject to any disclaimer, the term of this patent is extended or adjusted under 35 U.S.C. 154(b) by 1122 days.

(21) Appl. No.: 11/547,451

(22) PCT Filed: Apr. 1, 2005

(86) PCT No.: PCT/JP2005/006468
§ 371 (c)(1),
(2), (4) Date: May 25, 2007

(87) PCT Pub. No.: WO2005/097101
PCT Pub. Date: Oct. 20, 2005

(65) Prior Publication Data
US 2008/0044499 A1    Feb. 21, 2008

(30) Foreign Application Priority Data
Apr. 6, 2004 (JP) ................................. 2004-111726

(51) Int. Cl.
| | | |
|---|---|---|
| A61K 36/38 | (2006.01) | |
| A61K 36/00 | (2006.01) | |
| A61K 36/28 | (2006.01) | |
| A61K 31/045 | (2006.01) | |
| A23L 1/30 | (2006.01) | |
| A61K 31/405 | (2006.01) | |
| A61K 31/4045 | (2006.01) | |
| A61K 36/84 | (2006.01) | |
| A61K 31/198 | (2006.01) | |
| A61K 36/185 | (2006.01) | |
| A61K 31/197 | (2006.01) | |
| A61K 36/67 | (2006.01) | |
| A23L 1/305 | (2006.01) | |
| A61K 36/53 | (2006.01) | |

(52) U.S. Cl.
CPC ............. *A61K 31/197* (2013.01); *A61K 36/38* (2013.01); *A61K 31/045* (2013.01); *A23L 1/3002* (2013.01); *A61K 31/405* (2013.01); *A61K 31/4045* (2013.01); *A61K 36/84* (2013.01); *A61K 31/198* (2013.01); *A61K 36/185* (2013.01); *A61K 36/67* (2013.01); *A23L 1/3051* (2013.01); *A61K 36/28* (2013.01); *A61K 36/53* (2013.01)
USPC ............................ 424/730; 424/726; 424/764

(58) Field of Classification Search
None
See application file for complete search history.

(56) References Cited

U.S. PATENT DOCUMENTS

| | | | | |
|---|---|---|---|---|
| 5,641,801 | A * | 6/1997 | Wurtman | 514/415 |
| 6,579,543 | B1 * | 6/2003 | McClung | 424/728 |
| 6,589,566 | B2 * | 7/2003 | Ueda et al. | 424/617 |
| 2001/0001307 | A1 | 5/2001 | Ueda et al. | |
| 2002/0122835 | A1 * | 9/2002 | Bucci et al. | 424/729 |
| 2002/0151600 | A1 | 10/2002 | Nagashima et al. | |
| 2002/0188025 | A1 | 12/2002 | Ozeki et al. | |

FOREIGN PATENT DOCUMENTS

| | | | |
|---|---|---|---|
| CN | 1164422 | A * | 11/1997 |
| EP | 1275308 | A1 * | 1/2003 |
| JP | 08-169831 | A1 | 7/1996 |
| JP | 11-127781 | A1 | 5/1999 |
| JP | 2000-247878 | A1 | 9/2000 |
| JP | 2000247878 | A * | 9/2000 |
| JP | 2001-086954 | A1 | 4/2001 |
| JP | WO 01/74352 | A1 | 10/2001 |
| JP | 2002-306142 | A1 | 10/2002 |
| JP | 2003-164259 | A1 | 6/2003 |
| JP | 2003-183174 | A1 | 7/2003 |
| JP | 2003-334032 | A1 | 11/2003 |
| JP | 2003-335961 | A1 | 11/2003 |
| WO | WO 01/58435 | A1 | 8/2001 |

OTHER PUBLICATIONS

Cauffield et al, Dietary supplement used in the treatment of depression, anxiety, and sleep disorders, Lippincott's primary care practice, 1999; 3 (3): 290-304.*
New Japanese Journal of Ocular Pharmacology, 3rd Edition, Nankodo Co., Ltd., 1997, pp. 114-123.
Merck Manual, 16th Edition, Japanese Language Edition, Medical Book Service, 1985, pp. 1391-1393.

* cited by examiner

*Primary Examiner* — Qiuwen Mi
(74) *Attorney, Agent, or Firm* — Burr & Brown, PLLC (57) ABSTRACT

An object of this invention is to provide a sleep improvement composition, which contains theanine and other components and can be used safely by anybody on a daily basis without side effects. This object is attained by a sleep improvement composition comprising: (a) theanine; and (b) at least one component selected from the group consisting of chamomile, lavender, Saint John's wort, kawakawa, valerian, passion flower, tryptophan, γ-aminobutyric acid, serotonin, melatonin, and cedrol.

4 Claims, 1 Drawing Sheet

SLEEP IMPROVEMENT COMPOSITION

FIELD OF THE ART

This invention concerns a sleep improvement composition containing theanine, a food and a medical drug containing the same composition, a sleep improvement method using theanine, and the use of theanine for the manufacture of the above-mentioned food or medical drug.

BACKGROUND ART

Sleep, which takes up one-third of a person's life, is an important behavior for humans. However, in recent years, the influences of inadequate exercise in addition to stress and disruption of the daily rhythm of life, such as the inversion of night and day due to shifting of the hours of activity, have lead to an increase in the number of people complaining of inadequate sleep or insomnia, especially among city dwellers. Presently, it is said that one in five people have some form of dissatisfaction concerning sleep and one in ten people complain of insomnia of no less than one month. According to a field study concerning sleep disorders, the economic loss of Japanese citizens due to traffic accidents, etc., caused by sleep disorders is estimated at 1.4 trillion yen per year. It is furthermore estimated that for the nation of Japan as a whole, citizens spend 500 billion yen a year in medical expenses concerning sleep disorders, with medical costs spent on just sleeping drugs amounting to at least 182.5 billion yen.

The effects that various natural components have on sleep are widely known. For example, cedrol, which is a fragrance component that is contained in a conifer, such as Japanese cypress, cedar, etc., has been reported to have the effect of restraining the sympathetic nerves and making parasympathetic activity dominant and, in regard to sleep, is recognized to elongate the total sleeping time, shorten the sleep latency time, and increase the sleep efficiency (Patent Document 1). It is known that valerian, which is a Western herb, has a sedative effect and has been confirmed by human clinical tests to decrease the sleep latency time, improve the quality of sleep, elongate slow-wave sleep etc., (Non-Patent Document 1, Non-Patent Document 2).

Also, in tests using rats, Korean ginseng extract, which is widely used as a Chinese herbal medicine, has been reported to exhibit a sleep promoting effect, the effect of returning sleep, which has been changed in rhythm due to fasting, to a normal state, etc., (Non-Patent Document 3, Non-Patent Document 4). Furthermore, it has been reported that when 1-oleoyl-2-DHA-sn-3-phosphocholine, which is a phosphatidylcholine (PC) having DHA bonded to the sa-2 position and which, among the phosphatidylcholines contained in salmon roe oil, is a principle functional component in regard to sleep, is administered to a rat, the total sleeping time within 24 hours, the REM sleeping time, and the REM sleeping time with respect to the total sleeping time are increased (Non-Patent Document 5).

However, the abovementioned cedrol, which is a fragrance component of cedar, is a volatile substance and is thus difficult to use in the form of a food or medical drug that is taken orally. Also, research and development have not progressed much in regard to the details of the sleep improvement effects of valerian, Korean ginseng extract, and phosphatidylcholine.

[Non-Patent Document 1] Peter D. Leatherwood, Francoise Chaffard, Eva A Heck and Raphael Munoz-Box: Aqueous Extraction of Valerian Root (*Valeriana offcinalis* L.) improving Sleep Quantity in Man, Pharmacology Biochemistry & Behavior, Vol 17, pp. 65-71, 1982

[Non-Patent Document 2] Olov Lindahl and Lars Lindwall, Double Blind Study of a Valerian Preparation, Pharmacology Biochemistry & Behavior, Vol 32, pp. 1065-1066, 1989

[Non-Patent Document 3] Young Ho Rhee, Sung Pil Lee, Kazuki Honda, and Shojiro Inoue: *Panax ginseng* Extract Modulates Sleep in Unrestrained Rats, Psychopharmacology, 101, pp. 486-488, 1990

[Non-Patent Document 4] Sung Pil Lee, Kazuki Honda, Young Ho Rhee and Shojiro Inoue: Chronic Intake of *Panax ginseng*, Extract Stabilizes Sleep and Wakefulness in Food-deprived Rats, Neuroscinence Letters, 111, pp 217-221, 1990

[Non-Patent Document 5] Hidehiko Hibino, PC-DHA and Sleep, Food Style 2, Vol. 7, No. 3, pp. 50-53, 2003

[Patent Document 1] Republished Patent Publication No. WO01/058435

DISCLOSURE OF THE INVENTION

Problems to be Solved by the Invention

This invention has been made in view of the above circumstances and an object thereof is to provide a sleep improvement composition that is characterized in containing theanine and other concomitants. To be more detailed, an object of this invention is to provide a food and a medical drug to be applied to individuals with sleep disorder. A further object of this invention is to provide a sleep improvement method to be applied to individuals with sleep disorder and the use of theanine for the production of the abovementioned food or medical drug.

Means for Solving the Problems

Upon carrying out diligent research towards achieving the above object, the present inventors have found that by using (a) theanine and (b) at least one component selected from the group consisting of chamomile, lavender, Saint John's wort, kawakawa, valerian, passion flower, tryptophan, 5-HTP, serotonin, γ-aminobutyric acid, melatonin, and cedrol, the sleep promotion effect provided by theanine can be exhibited more effectively and that such combined use does not accompany any problematic side-effects and have thereby been lead to complete the present invention.

This invention concerns: [1] asleep improvement composition comprising: (a) theanine; and (b) at least one component selected from the group consisting of chamomile, lavender, Saint John's wort, kawakawa, valerian, passion flower, tryptophan, 5-HTP, serotonin, γ-aminobutyric acid, melatonin, and cedrol;

[2] the sleep improvement composition according to [1], wherein the sleep improvement effect improves sleepiness upon arising;

[3] the sleep improvement composition according to [1], wherein the sleep improvement effect is the extension of sleeping time;

[4] a food containing the composition according to any of [1] to [3];

[5] a medical drug containing the composition according to any of [1] to [4];

[6] a sleep improvement method characterized in administering a composition comprising: (a) theanine; and (b) at least one component selected from the group consisting of chamomile, lavender, Saint John's wort, kawakawa, valerian, passion flower, tryptophan, 5-HTP, serotonin, γ-aminobutyric acid, melatonin, and cedrol; and

[7] the use of (a) theanine and (b) at least one component selected from the group consisting of chamomile, lavender, Saint John's wort, kawakawa, valerian, passion flower, tryptophan, 5-HTP, serotonin, γ-aminobutyric acid, melatonin, and cedrol for manufacturing a food or a medical drug to be applied to individuals with sleep disorder.

EFFECTS OF THE INVENTION

This invention's sleep improvement composition (may be referred to hereinafter simply as "composition") can be used on a daily basis for the purpose of alleviating or improving on various sleep disorders caused by various causes. By this invention's composition, at least one or more symptoms of sleep disorders can be improved. As improvement effects concerning sleep disorder symptoms, for example, at least one selected from among the group consisting of "sleepiness upon arising," "alleviation of fatigue upon arising," "extension of sleeping time," "improvement of sleep onset," "improvement of dream quality," "reduce of intermingled awakening," "reduce of intermingled awakening during the latter half of sleep," and "improvement of sleep efficiency," can be cited. Among these, effects were seen especially in regard to improving on "sleepiness upon arising" and "extension of sleeping time."

The exhibiting of the desired effects of this invention's composition are based on sleep improvement effects that have been found for the first time in the combined use of (a) theanine and (b) at least one component selected from the group consisting of chamomile, lavender, Saint John's wort, kawakawa, valerian, passion flower, tryptophan, 5-HTP, serotonin, γ-aminobutyric acid, melatonin, and cedrol, which are contained in the composition.

BEST MODES FOR CARRYING OUT THE INVENTION

Though embodiments of this invention shall now be described in detail, the scope of the art of this invention is not limited by the following embodiments and various modifications are possible without deviating from the gist of the present invention. The scope of the art of this invention covers the scope of equivalents.

Theanine, which is used in this invention, is a monosodium glutamate derivative contained in tea leaves, is a main component of the savory of tea, and is used as a food additive for providing flavor. Methods of producing theanine, which is used in this invention, include, for example, methods of extraction from tea leaves, a method of obtaining theanine by organic synthesis reaction (Chem. Pharm. Bull., 19 (7) 1301-1307 (1971)), a method of obtaining theanine by making glutaminase react on a mixture of glutamine and ethylamine (Japanese Published Examined Patent Application No. H7-55154), a method of culturing a cultured cell cluster of tea in a medium containing ethylamine and promoting the proliferation of the cultured cell cluster while increasing the theanine accumulation amount in the cultured cell cluster (Japanese Published Unexamined Patent Application No. H5-123166), methods of obtaining theanine by replacing the ethylamine in Japanese Published Examined Patent Application No. H7-55154 or Japanese Published Unexamined Patent Application No. H5-123166 by ethylamine hydrochloride or other ethylamine derivative, and methods of extraction from tea leaves, etc., and theanine may be obtained from any of these methods or may be produced by methods besides these methods. Green tea, oolong tea, black tea, etc., can be cited as examples of tea leaves.

Though the L-isomer, D-isomer, and DL-mixtures of theanine, obtained by such methods, can all be used, among these, since the L-isomer is approved as a food additive and can be readily used in economic terms as well, the use of the L-isomer is preferable.

This invention's composition is not limited in particular in terms of administration method, number of times of administration, administration period, etc., and can be administered once or in a plurality of times by a suitable form of administration and preferably by oral administration to humans, preferably, humans desiring alleviation or improvement of sleep disorders. This invention's composition can also be taken on a daily basis to prevent sleep disorders.

Theanine, which is used in this invention, is highly safe, and, for example, in acute toxicity tests using mice, even at an oral administration of 5 g/kg, there were no cases of death and no abnormalities were seen in general conditions, body weight, etc. In particular, theanine is known as a "umami" component of tea, is used as a food additive for providing flavor, and the Food Sanitation Law places no restrictions in addition amount. Since unlike conventional drugs, theanine does not exhibit side effects at all, this invention's composition can be used safely and effectively as a sleep improvement composition.

As described above, from the standpoint of safety, there is no upper limit to the dosage of theanine. However, in terms of economy and actual intake, the dosage of theanine at one time is 0.01 mg/kg body weight to 100 mg/kg body weight, preferably 0.1 mg/kg body weight to 80 mg/kg body weight, and more preferably 1 mg/kg body weight to 50 mg/kg body weight. The theanine used in this invention may be of any form, such as purified product (with a theanine content of no less than 98%), crudely purified product (with a theanine content of 50% to 98%), extract (with a theanine content of 10% to 50%), etc.

As a concomitant of (a) theanine, (b) at least one component selected from the group consisting of chamomile, lavender, Saint John's wort, kawakawa, valerian, passion flower, tryptophan, 5-HTP, serotonin, γ-aminobutyric acid, melatonin, and cedrol (these components shall hereinafter be referred to as "the other components") can be cited, and these can be classified into (A) herbs, that is, chamomile, lavender, Saint John's wort, kawakawa, valerian, and passion flower, (B) chemical compounds, that is, tryptophan, 5-HTP, serotonin, γ-aminobutyric acid, and melatonin, and (C) fragrance component, that is, cedrol.

(A) Herbs

Chamomiles are plants of the family Compositae that originate in Europe and are among the oldest herbs that have been used since the times of ancient Egypt. The annual German chamomile, the perennial Roman chamomile, etc., are known among chamomiles, and any of these may be used in this invention. The dosage of chamomile at one time is 0.004 mg/kg body weight to 6000 mg/kg body weight, preferably 0.6 mg/kg body weight to 4800 mg/kg body weight, and more preferably 0.6 mg/kg body weight to 1500 mg/kg body weight. When theanine and chamomile are used in combination, the mass ratio of chamomile to theanine is in the range of 0.4 to 60, preferably in the range of 6 to 60, and more preferably in the range of 6 to 30.

Lavender is a well-known herb and comes in numerous varieties. English lavender and French lavender can be cited as representative examples and any of such lavenders can be used in this invention. The dosage of lavender at one time is 0.003 mg/kg body weight to 3000 mg/kg body weight, preferably 0.2 mg/kg body weight to 600 mg/kg body weight, and more preferably 2 mg/kg body weight to 600 mg/kg body weight. When theanine and lavender are used in combination, the mass ratio of lavender to theanine is in the range of 0.3 to 30, preferably in the range of 2 to 12, and more preferably in the range of 2 to 6.

Saint John's wort is a perennial (hypericum) of the family Hypericaceae and has been used as of old in Europe. The dosage of St John's wort at one time is 0.001 mg/kg body weight to 2000 mg/kg body weight, preferably 0.2 mg/kg body weight to 480 mg/kg body weight, and more preferably 1 mg/kg body weight to 150 mg/kg body weight. When theanine and St John's wort are used in combination, the mass ratio of St John's wort to theanine is in the range of 0.1 to 20, preferably in the range of 2 to 6, and more preferably in the range of 1 to 3.

Kawakawa is an herb of the family Piperaceae that originates in Polynesia and is used by people inhabiting the Oceanic islands of Micronesia, Polynesia, Melanesia, etc. The dosage of kawakawa at one time is 0.0002 mg/kg body weight to 1000 mg/kg body weight, preferably 0.04 mg/kg body weight to 160 mg/kg body weight, and more preferably 0.4 mg/kg body weight to 160 mg/kg body weight. When theanine and kawakawa are used in combination, the mass ratio of kawakawa to theanine is in the range of 0.02 to 10, preferably in the range of 0.4 to 2, and more preferably in the range of 0.4 to 1.

Valerian is a plant of the family Valerianaceae that originates in Europe and contains valeranone, valerenic acid, etc. The dosage of valerian at one time is 0.002 mg/kg body weight to 4000 mg/kg body weight, preferably 0.4 mg/kg body weight to 1600 mg/kg body weight, and more preferably 2 mg/kg body weight to 500 mg/kg body weight. When theanine and valerian are used in combination, the mass ratio of valerian to theanine is in the range of 0.2 to 40, preferably in the range of 2 to 20, and more preferably in the range of 4 to 10.

Passion flower is a perennial vine of the family Passifloraceae that originates in the southwestern part of North America and is an herb that has been used traditionally by native North Americans as a natural tranquilizer for relaxing tension and deepening sleep. The dosage of passion flower at one time is 0.002 mg/kg body weight to 8000 mg/kg body weight, preferably 0.5 mg/kg body weight to 1040 mg/kg body weight, and more preferably 5 mg/kg body weight to 500 mg/kg body weight. When theanine and passion flower are used in combination, the mass ratio of passion flower to theanine is in the range of 0.2 to 80, preferably in the range of 5 to 13, and more preferably in the range of 5 to 10.

(B) Chemical Compounds

Tryptophan is a type of amino acid and is a source of serotonin, which is an endogenous sleep chemical, and melatonin, which is called a sleep hormone. The dosage of tryptophan at one time is 0.0005 mg/kg body weight to 10000 mg/kg body weight, preferably 0.01 mg/kg body weight to 1600 mg/kg body weight, and more preferably 1 mg/kg body weight to 100 mg/kg body weight. When theanine and tryptophan are used in combination, the mass ratio of tryptophan to theanine is in the range of 0.05 to 100, preferably in the range of 0.1 to 20, and more preferably in the range of 1 to 2.

5-HTP (5-hydroxytryptophan) is a substance that is formed when tryptophan enters the brain and is a precursor of serotonin. The dosage of 5-HTP at one time is 0.005 mg/kg body weight to 1000 mg/kg body weight, preferably 0.01 mg/kg body weight to 400 mg/kg body weight, and more preferably 1 mg/kg body weight to 150 mg/kg body weight. When theanine and 5-HTP are used in combination, the mass ratio of 5-HTP to theanine is in the range of 0.5 to 10, preferably in the range of 0.1 to 5, and more preferably in the range of 1 to 3.

Serotonin is a neurotransmitter in the brain that controls a wide range of physiological functions including awakening, sleep, locomotor activity, eating, water drinking behavior, aggressiveness, learning and memory abilities, sexual behavior, central blood pressure adjustment, etc., and it is said that when the serotonin level decreases, anxiety, sleep disorders, depressive symptoms, etc., occur. The dosage of serotonin at one time is 0.005 mg/kg body weight to 1000 mg/kg body weight, preferably 0.01 mg/kg body weight to 400 mg/kg body weight, and more preferably 1 mg/kg body weight to 150 mg/kg body weight. When theanine and serotonin are used in combination, the mass ratio of serotonin to theanine is in the range of 0.1 to 10, preferably in the range of 0.5 to 5, and more preferably in the range of 1 to 3.

γ-aminobutyric acid (GABA) is an amino acid that is widely found among animals and plants and is a suppressive neurotransmitter that exists in the brain and medulla of mammals. GABA is said to exhibit such effects as suppression of blood pressure increase, suppression of increase of neutral fats, improvement of blood flow in the brain, increase of blood flow into organs, sedation of the central nervous system, etc. The dosage of γ-aminobutyric acid at one time is 0.0005 mg/kg body weight to 10000 mg/kg body weight, preferably 0.01 mg/kg body weight to 1600 mg/kg body weight, and more preferably 1 mg/kg body weight to 100 mg/kg body weight. When theanine and γ-aminobutyric acid are used in combination, the mass ratio of γ-aminobutyric acid to theanine is in the range of 0.05 to 100, preferably in the range of 0.1 to 20, and more preferably in the range of 1 to 2.

Melatonin is a hormone that is secreted from the pineal body in the human brain and the amount of secretion is adjusted in accordance to the brightness or darkness of the surroundings (that is, more is secreted in dark surroundings and less is secreted in bright surroundings). It is thus considered to synchronize the functions of mammals to the photoperiod of the environment. The dosage of melatonin at one time is 0.005 mg/kg body weight to 1000 mg/kg body weight, preferably 0.01 mg/kg body weight to 400 mg/kg body weight, and more preferably 1 mg/kg body weight to 150 mg/kg body weight. When theanine and melatonin are used in combination, the mass ratio of melatonin to theanine is in the range of 0.1 to 10, preferably in the range of 0.5 to 5, and more preferably in the range of 1 to 3.

(C) Fragrance Component

Cedrol is a natural fragrance component of wood that is contained in *cryptomeria*, Japanese cypress, etc. Since cedrol is a volatile component, it is preferably made a volatilizing substance that can be taken in from the nose. The concentration of cedrol in air is 0.01 μg/L to 100 μg/L, preferably 0.1 μg/L to 10 μg/L, and more preferably 0.5 μg/L to 5 μg/L.

The composition of this invention may be consumed as it is, as a dry food, a supplement, or a liquid food, such as a soft drink, mineral water, nonessential beverage, alcohol drink, etc., in a dosage form such as tablets, capsules, powder, granules, drinkable preparation, etc., or as a volatilizing substance.

With the present invention, sleep improvement means that the sleep sensation is improved according to subjective judgment using psychological evaluation techniques or that the sleep state is improved objectively as judged by techniques of estimating sleep and wakefulness states based on continuous recording of activity amounts.

As diagnosis methods used for judging sleep states, there are the three diagnostic classifications of the International Classification of Sleep Disorders, prepared mainly by the American Sleep Disorders Association, the sleep disorder items in the Diagnostic and Statistical Manual of Mental Disorders (DMS-IV), prepared by the American Psychiatric Association, and the sleep disorder items in the ICD, which are the diagnostic standards of WHO, and these list numerous names of sleep disorders.

With the present invention, sleep sensation refers to a subjective sensation concerning sleep or an introspective report concerning the depth of sleep or the sensation of one night's sound sleep. The sleep sensation is a psychological attitude towards sleep that is unique to each individual and is an assemblage of judgment results concerning the three levels of emotion, cognition, and activity. The OSA sleep questionnaire can be used to examine the sleep sensation of the previous night to the present morning upon arising. The OSA sleep questionnaire is a questionnaire in which introspection concerning sleep is standardized, and is available as the 1st version, 2nd version, and the MA version. The MA version of the OSA sleep questionnaire (referred to herein after as "OSA-MA;" Yukari Yamamoto, Hideki Tanaka, Miki Takahashi, Masao Yamazaki, Kazuo Azumi, and Shuichiro Shirakawa: Development and standardization of the OSA sleep questionnaire (MA version) for middle aged and elderly people, Brain Science and Mental Disorders, vol. 10, pp. 401-409, 1999) is based on the five factors of sleepiness upon arising, sleep initiation and sleep maintenance, dream quality, recovery from fatigue, and elongation of sleep length and has been verified in regard to the reliability and validity of the respective factors.

With the present invention, fatigue mainly refers to mental fatigue, and if the sleep state is good, one feels recovery from fatigue upon arising. Fatigue refers to the phenomenon of the lowering of a function of a living body when the living body exerts a function or the decline of working ability or exercise ability upon exertion of strength or performing of exercise. Recovery from fatigue refers to the returning from the state of lowered function to the level that a living body has originally. The fatigue of a living body is classified into physical fatigue of the muscles and mental fatigue of the brain, sensory system, etc., and sleep mainly serves an important role in the recovery of the brain from mental fatigue.

With the present invention, the sensation of elongation of the sleep length does not refer to the actual sleeping time but refers to the subjective awareness of elongation of the sleep length. Reduce of intermingled awakening and improvement of early morning awakening are considered to be factors by which elongation of the sleep length is felt.

With this invention, improvement of sleep onset refers to the improvement of the psychological evaluation concerning falling asleep in the sleep onset process, and the sleep onset process refers to the state from the point of lying down on a bed to the point of falling asleep. A sleep onset disorder, which is cited among the classification of insomnia, is an extension of time from the point at which an individual consciously intends to fall asleep to the point of actually falling asleep and is often seen in insomnia. This means that the present invention improves sleep onset disorders. Though causes of insomnia include the opportunistic use of drugs that bring about insomnia and the excessive intake of caffeine or nicotine, sleep onset disorders due to these causes are not included here.

With the present invention, improvement of dream quality refers to the restraining of seeing nightmares and the reduce of the frequency of dreaming. A nightmare is a phenomenon of waking up due to extreme anxiety and fear associated with a vivid dream seen at night, at times in accompaniment with screaming and fluctuation of the autonomic nerves. Upon awakening, the contents of the dream can be remembered in detail, the consciousness is clear, and immediate adaptation to the surroundings is enabled. Nightmares have the characteristic of tending to occur during REM sleep from halfway during night sleep towards the morning. A nightmare is a clear dream, filled with fear and anxiety that threaten life, security, or self-respect, and, for example, is a dream of being chased, robbed, raped, about to be killed, pushed off from a building, etc., and awakening from the dream occurs due to the fear. Most nightmares are long, convoluted, and increases in fear towards the end of the dream. The awakening from such a dream of fear is an awakening from REM sleep and thus tends to occur at the latter half of sleep. After awakening, the sense of orientation and consciousness become clear rapidly and though a long and fearful dream can be recalled in detail, one cannot fall asleep again readily due to the fear.

With this invention, dreaming refers to a subjective symptom occurring during sleep that accompanies a clear sensational image, and is a state wherein the control action of consciousness is weakened extremely. Dreaming occurs at a high probability in the REM sleep stage. Whereas the percentage of dream recall upon awakening in the REM sleep stage is no less than 80%, the dream recall percentage in the non-REM stage is only 7%. During REM sleep, rapid eye movement, atony of the skeletal muscles, and sudden cramping are seen and the cerebral cortex is partially activated and exhibits brain waves similar to those seen in the awakened state. As a form of sleep, the REM sleep stage is a state of shallow sleep and frequent dreaming means that dreams are seen frequently due to the sleep in the early morning being shallow.

With this invention, sleeping time refers to the time from sleep onset to arising and signifies the time with which the sleep latency time is subtracted from the total bedding time. The total bedding time is the time from lying on a bed to arising, and the sleep latency time is the time from lying on a bed to sleep onset. Sleep onset refers to the case where sleep stage 1 is sustained for no less than 90 seconds. The sleeping time can be measured by a sleep polygraph or an actigraph.

With this invention, intermingled awakening refers to the awakening in the middle of the night and not being able to sleep thereafter or the state of not feeling as if one had a sound sleep as a result of the quality of sleep being poor due to awakening more frequently than the average. With elderly people, since sleep is shallow, intermingled awakening tends to occur readily and the quality of sleep as a whole is thereby lowered. Intermingled awakening can be observed quantitatively by a sleep polygraph or an actigraph.

With this invention, the latter half of sleep refers to the time period closer to the time of arising when the sleeping time is divided in half. The latter half of sleep is characterized in that REM sleep is often seen in this stage.

With this invention, sleep efficiency refers to the proportion of the time of actual sleeping with respect to the time in bed. The sleep efficiency becomes poor when intermingled awakening occurs.

In regard to subjects, this invention's composition can be applied to humans diagnosed with sleep disorders, humans who are not satisfied with their own sleep, etc. A sleep disorder refers to a state, wherein symptoms, such as a sleep onset disorder, intermingled awakening, early morning awakening, lack of sound sleep sensation, etc., occur at least three times a week and continue for no less than one month and sleep is obstructed qualitatively and quantitatively, and can be diagnosed and classified according to the International Classification of Sleep Disorders (ICSD), the classification of sleep disorders according to DSM-IV, the classification of sleep disorders according to ICD-10, etc. This invention is especially effective for humans who, among those that are affected by sleep disorders, are affected by insomnia. Here insomnia refers to the sleep onset disorder of not being able to fall asleep readily self-consciously, the intermingled awakening disorder of frequently awakening in the middle of sleep, the early morning awakening disorder of undesirably awakening early in the morning, and the sound sleep disorder of feeling as if not having slept. This invention is also effective for nightmares.

The state of not being satisfied with one's own sleep refers to cases where one subjectively feels dissatisfaction with one's own sleep and to cases where, even though the diagnostic standards of insomnia are not met, the symptoms of sleep onset disorder, intermingled awakening, early morning awakening, lack of sound sleep sensation, etc., are seen on rare occasions.

Though the subjects of this invention are mainly humans, this invention can also be applied to other animals that are known to sleep (for example, dogs, cats, cattle, horses, hamsters, guinea pigs, rats, mice, and other mammals, parakeets, parrots, society finches, and other birds, etc.).

This invention's composition is used favorably, for example, as a food or a medical drug. Such a food is not restricted in particular, and dry foods or other solid foods, supplements, and liquid foods, such as soft drinks, mineral water, nonessential beverages, alcohol drinks, etc., that contain (a) theanine and (b) the other components can be cited as examples. As medical drugs, those of various dosage forms, such as tablets, capsules, powders, granules, drinkable preparations, etc., can be cited as examples.

Though the form of the food that contains this invention's composition is not restricted in particular, the normal chewable forms, tablet forms, capsule forms, granular forms, powder forms, drink forms, etc., can be cited as examples.

Examples of the abovementioned solid foods include kneaded products, processed soy products, mousses, jellies, yogurts, frozen desserts, candies, chocolates, gums, crackers, biscuits, cookies, cakes, breads, etc. Examples of liquid foods include teas, such as green tea, oolong tea, black tea, herb tea, etc., concentrated fruit juices, from-concentrate juices, straight juices, mixed fruit juices, fruit juices with fruit bits, fruit-juice-containing drinks, fruit and vegetable mixture juices, vegetable juices, carbonated drinks, soft drinks, milk beverages, etc. In the case where (b) the other components are selected from among (A) herbs, a liquid food is preferable and an herb tea is more preferable.

Though the amount of theanine contained in the composition is not restricted in particular, it is in the range of 0.001% to 99.9%, preferably 0.01% to 99%, and more preferably in the range of 0.1% to 90%.

With this invention's composition, natural medicines, herbs, amino acids, vitamins, minerals, and other raw materials and ingredients that are approved for foods can be used in combination. Here, the natural medicines used are not restricted in particular, and Japanese valerian, Japanese angelica root, peony root, moutan, Korean ginseng, etc., can be cited as examples.

The herbs are not restricted in particular, and anise, carrot seed, clove, coriander, cypress, cinnamon, juniper, ginger, sweet orange, pine needles, basil, patchouli, bitter orange, fennel, black pepper, bay, peppermint, bergamot, mandarin, myrrh, lemon grass, rosemary, grapefruit, vanilla, hyssop, eucalyptus, lime, lemon, ylang-ylang, cardamom, clary sage, jasmine, geranium, Bulgarian rose, rose, olibanum, chamomile, geranium, sandalwood, neroli, verbena, petitgrain, vetiver, majorum, melissa, rosewood, etc., can be cited as examples. Among these, peppermint is preferable. Examples of the forms of these herbs include extracts, essential oils, herb teas, etc.

The amino acids are not restricted in particular, and glutamine, monosodiumglutamate, inosinic acid, alanine, arginine, aspartic acid, threonine, serine, taurine, thiotaurine, hypotaurine, etc., can be cited as examples.

The vitamins are not restricted in particular, and vitamin A, vitamin B1, vitamin B2, vitamin B6, vitamin B12, vitamin C, vitamin D, vitamin E, vitamin K, folic acid, nicotinic acid, lipoic acid, pantothenic acid, biotin, ubiquinone, etc., can be cited as examples. Among these, vitamin B1, vitamin B6, and vitamin B12 are preferable. Derivatives of the respective vitamins are also included.

The minerals are not restricted in particular, and calcium, iron, magnesium, copper, zinc, selenium, potassium, etc., can be cited as examples.

Examples of other raw materials and ingredients approved for use in foods include peptides, carotenoids, aloe, royal jelly, placenta, propolis, isoflavone, soybean lecithin, egg yolk lecithin, egg yolk oil, chondroitin, cacao mass, collagen, vinegar, *chlorella*, spirulina, gingko leaf, green tea, du zhong tea, Chinese wolfberry tea, oolong tea, mulberry leaf, Chinese blackberry tea, banaba tea, unsaturated fatty acids, saccharides such as sugar alcohols and oligosaccharides, bacteria and fungi such as bifidobacteria and red koji, mushrooms such as *Agaricus, Agaricus blazei, ganoderma*, and *Grifola frondosa*, fruits, such as blueberry, prune, grape, olive, Japanese plum, and citruses, seeds such as peanuts, almonds, sesame, and pepper, vegetables, such as green pepper, chili, Welsh onion, pumpkin, melon, carrot, great burdock, mulukhiya, garlic, *perilla*, wasabi, tomato, scallion, leaf vegetables, tubers, and beans, seaweeds, such as wakame seaweed, etc., fishes, animal meat, poultry, whale meat, cereals, etc., and extracts, dried products, crudely purified products, purified products, processed products, fermented products, etc., of such raw materials and ingredients may also be used.

The form of use as a medical drug is not restricted in particular, and orally administered drugs, injection drugs, transdermal application drugs, suppositories, inhaled drugs, etc., can be cited as examples. Examples of forms of orally administered drugs include the conventionally used forms of tablets, capsules, granules, drinkable preparations, etc. Examples of forms of injection drugs include intramuscular injection drugs, intradermal injection drugs, subcutaneous injection drugs, intravenous injection drugs, etc. A transdermal application drug, which is prepared by coating a sheet, etc., used in known transdermal application drugs, with a blend of the effective components of this invention and a known carrier, conventionally used in the manufacture of transdermal application drugs, etc., can be cited as an example of a transdermal application drug. A suppository, which is prepared by blending this invention's composition with a conventionally used cacao fat, glycerogelatin, sodium stearate, propylene glycol monostearate, etc., can be cited as an example of a suppository. An inhalation drug, which is inhaled by a conventional method and has a dosage form that can be absorbed from the nasal aperture or oral cavity along with water vapor or air, etc., can be cited as an example of an inhalation drug.

Green tea extracts can be used in combination with this invention's sleep improvement composition. A green extract used in this invention contains catechins (A) at an amount of 0.001% to 90%, preferably 0.001% to 85%, and more preferably 0.1% to 80%. The catechins (A) contained in the green tea extract refer generally to non-epi catechins (B), such as catechin, gallocatechin, catechin gallate, gallocatechin gallate, etc., and epicatechins (C), such as epicatechin, epigallocatechin, epicatechin gallate, epigallocatechin gallate, etc., (that is, A=B+C). In regard to the composition of the catechins in the present invention, the contained weight ratio of non-epi catechins (B) to epicatechins (C) is such that non-epi catechins/epicatechins (B/C) is 0.25 to 9.0, preferably 0.43 to 9.0, more preferably 0.43 to 5.67, and especially preferably 0.54 to 5.67. The dosage of the green tea extract at one time is 0.0005 mg/kg body weight to 10000 mg/kg body weight, preferably 0.01 mg/kg body weight to 1600 mg/kg body weight, and more preferably 1 mg/kg body weight to 100 mg/kg body weight. In cases were theanine (A) and green tea extract (D) are to be used in combination, the weight ratio of green tea extract to theanine (D/A) is 0.05 to 100, preferably 0.1 to 20, and more preferably 1 to 2.

The method of preparing this invention's composition is not restricted in particular as long as it includes a step of blending theanine and the other components. A preparation method of mixing powders of theanine and other raw materials (including the other components), a preparation method of dissolving theanine and other raw materials in a solvent and thereby preparing a mixed solution, a preparation method of freeze drying or spray drying such a mixed solution, and other generally used preparation methods for foods and medical drugs can be cited as examples.

Though examples of product forms of this invention include solutions, suspensions, powders, formed solids, etc., the product forms are not restricted to these. As forms of food, in addition to the forms of solid foods and liquid foods given above as examples, such forms as seasoning, soup, coffee, cocoa, milk products, etc., can also be cited as examples. As forms of medical drugs, the forms of tablets, capsules, injection drugs, etc., prepared by blending the composition of this invention and other concomitants with a suitable, known carrier, which is suitably selected in accordance to application, dosage form, etc., can be cited.

EXAMPLES

Though the present invention shall now be described in further detail by way of examples, the scope of this invention is not restricted to just these examples. In the following description, "mg/kg" shall indicate the dosage in units of mg per 1 kg of body weight.

Reference Example 1

Production of Theanine by an Enzymatic Method

By reacting 0.3M glutamine and 1.5M ethylamine hydrochloride in 0.05M borate buffer (pH 11) at 30° C. for 22 hours under the presence of 0.3 U glutaminase (commercially available product), 225 nmol of theanine were obtained. The reaction solution was then subject to chromatography using Dowex 50×8 and Dowex 1×2 columns (both made by Muromachi Technos Co., Ltd.) and to ethanol treatment to isolate the target substance from the reaction solution. 8.5 g of theanine were thus obtained.

The isolated substance was then subject to an amino acid analyzer (made by Hitachi, Ltd.) and paper chromatography and, by exhibition of the same behavior as a standard substance, was confirmed to be L-theanine. Upon hydrolytic treatment with hydrochloric acid or glutaminase, monosodium glutamate and ethylamine were produced at a ratio of 1:1. That the isolated substance is hydrolyzed by glutaminase indicates that ethylamine is bonded to the γ position of monosodium glutamate. That the monosodium glutamate resulting from hydrolysis is the L-isomer was confirmed by means of monosodium glutamate dehydrogenase.

Reference Example 2

Extraction of Theanine from Tea Leaves

After extraction of 10 kg of tea (*Camellia sinensis*) leaves in hot water, the extract was passed through a cation exchange resin (Dowex HCR W-2, made by Muromachi Technos Co., Ltd.) and eluted with 1N NaOH. The eluted fraction was then passed through activated carbon (Taiko Activated Carbon SG, made by Futamura Chemical Co., Ltd.) and the eluted fraction eluted with 15% ethanol was concentrated using an RO film (NTR 729 HF, made by Nitto Denko Co., Ltd.), purified by column chromatography, and then recrystallized. 24.8 g of theanine were thus obtained.

In the respective tests and production of the respective compositions described below, theanine (product name: Sun theanine, made by Taiyo Kagaku Co., Ltd.) was used.

Example 1

Production of Tablets Containing Theanine and Chamomile

As an example of the sleep improvement composition, the raw materials shown in Table 1 below were mixed and formed into tablets to produce tablets in which theanine and chamomile are blended.

TABLE 1

| Material | Weight % | Weight (mg) |
| --- | --- | --- |
| Theanine | 5.0 | 50.00 |
| Chamomile | 50 | 500 |
| Enzymolysis product of guar gum | 1.7 | 17.00 |
| Crystalline cellulose | 0.75 | 7.50 |
| Reduced maltose syrup powder | 5.0 | 50.00 |
| Lactose | 36.675 | 366.75 |
| Silicon dioxide | 0.125 | 1.25 |
| Sucrose fatty acid ester | 0.75 | 7.50 |
| Total | 100 | 1000 |

The respective raw materials were mixed in accordance to the composition and after being formed into granules, the mixture was formed into tablets of 1000 mg per tablet.

Examples 2 to Examples 11

Besides adding lavender, Saint John's wort, kawakawa, valerian, passion flower, tryptophan, 5-HTP, serotonin, γ-aminobutyric acid, or melatonin by the weight % indicated in Table 2 below in place of chamomile in Example 1, the same operations as those of Example 1 were performed to form tablets of 1000 mg per tablet (the tablets of Examples 1 to 11 shall hereinafter be referred to as "test tablets").

TABLE 2

| Example | Chamomile substitute | Added weight % |
| --- | --- | --- |
| 2 | Lavender | 25 |
| 3 | Saint John's wort | 10 |
| 4 | Kawakawa | 5 |
| 5 | Valerian | 25 |
| 6 | Passion flower | 25 |

TABLE 2-continued

| Example | Chamomile substitute | Added weight % |
|---|---|---|
| 7 | Tryptophan | 5 |
| 8 | 5-HTP | 10 |
| 9 | Serotonin | 10 |
| 10 | γ-aminobutyric acid | 5 |
| 11 | Melatonin | 5 |

Example 12

With cedrol, which is a volatile component, a combined-used test was conducted in which cedrol of an amount calculated to provide a cedrol concentration in air of approximately 1 μg/L was taken along with the theanine-containing tablets of Comparative Example 1 described below.

Comparative Example 1

Production of Control Tablets

As a comparative example, the raw materials shown in Table 3 below were mixed and formed into tablets to produce control tablets.

TABLE 3

| Material | Weight % | Weight (mg) |
|---|---|---|
| Theanine | 5.0 | 50.00 |
| Enzymolysis product of guar gum | 2.5 | 25.00 |
| Crystalline cellulose | 0.75 | 7.50 |
| Reduced maltose syrup powder | 5.0 | 50.00 |
| Lactose | 85.875 | 858.75 |
| Silicon dioxide | 0.125 | 1.25 |
| Sucrose fatty acid ester | 0.75 | 7.50 |
| Total | 100 | 1000 |

The respective raw materials were mixed in accordance to the above composition and after being formed into granules, the mixture was formed into tablets of 1000 mg per tablet.

Test Example 1 Selection of Test Subjects

The test subjects were 13 healthy, day-working males of age 25 to 36 (28.6±1.1) and 13 healthy male university students of age 20 to 33 (26.8±1.3), who agreed to cooperate upon receiving adequate explanation concerning the research details. The test subjects were subject in advance to the Moseley personality inventory, the CMI health examination, and a sleep heath questionnaire to confirm that they had neither illnesses that were being treated nor past history that would present a problem, no significant bias in personality, and no significant problems in sleep health.

Test Example 2

Validation of Sleep Improvement Effect

During the test period, the test subjects were instructed to lead an orderly lifestyle and were requested to keep their bedding time and arising time substantially the same both during holidays and working days so that these times would not deviate from the subjects' normal bedding and arising times by more than an hour. The test subjects were also instructed to take meals in orderly fashion, not to take medicines and large amounts of alcohol, and to refrain from drinking coffee, black tea, green tee, oolong tea, health drinks and other caffeine-containing drinks after dinner. The test subjects were instructed to take a nap as much as possible and prohibited from taking trips that would accompany a change of bed and from performing excessive exercise and swimming that would deviate from normal daily activities.

Figure 1:
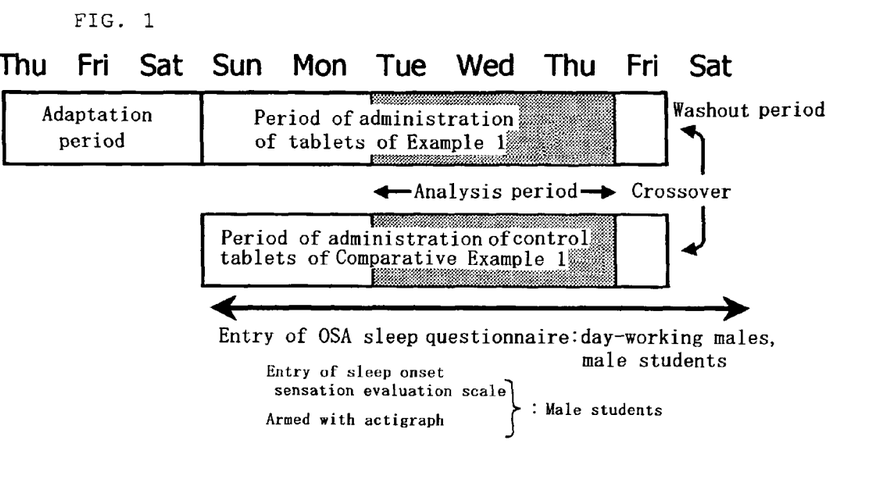
[FIG. 1] A diagram of an experimental schedule.

As the experimental schedule, the lifestyle adaptation period was set to 3 days, the administration period was set to 6 days each for the test tablets of Example 1 and the control tablets of Comparative Example 1, and a 1-day effect elimination period was taken between the administration of the test tablets of Example 1 and the administration of the control tablets of Comparative Example 1. A crossover design, based on counterbalance for eliminating order effects, was applied to the administration conditions of the test tablets of Example 1 and the control tablets of Comparative Example 1 (FIG. 1).

The test subjects selected in Test Example 1 were instructed to take four test tablets of Example 1 with water one hour prior to the habitual bedding time during the period of administration of the test tablets of Example 1. During the period of administration of the control tablets of Comparative Example 1, the test subjects were instructed to take the control tablets of Comparative Example 1 in the same manner. At the arising times of consecutive days during the test period, daily introspective sleep evaluations and psychological evaluations were made using the MA version of the OSA sleep questionnaire (Yukari Yamamoto, Hideki Tanaka, Miki Takahashi, Masao Yamazaki, Kazuo Azumi, and Shuichiro Shirakawa Development and standardization of the OSA sleep questionnaire (MA version) for middle aged and elderly people, Brain Science and Mental Disorders, vol. 10, pp. 401-409, 1999). The MA version of the OSA sleep questionnaire, which serves as a main part of the evaluation of effects on sleep, is made up of 16 question items and is standardized. This questionnaire is statistically categorized into five factors, that is, the first factor of sleepiness upon arising, the second factor of sleep initiation and sleep maintenance, the third factor of dream quality, the fourth factor of recovery from fatigue, and the fifth factor of elongation of sleep length. For evaluation of the psychological state upon arising, hearings using a four-choice selection method were conducted concerning motivation, feeling, and self-confidence. Whether or not there were any days deviating from normal life during the test period was checked by means of daily reports concerning sleep and daily living prior to bedding.

Also, with each of the male university students, an actigraph (made by A.M.I. Corp., USA) was armed on the non-dominant wrist constantly at times besides times of bathing and working with water to continuously record activity amounts at each minute and, at the same time, a standardized sleep onset sensation evaluation scale was applied. From the continuous activity amounts recorded by the actigraphs, sleep and wake were identified in accordance to the method of Cole and others (Cole Rj, Kripke D F, Gruen W, et al.: Automatic sleep/wake identification from wrist activity. Sleep., vol. 15, pp. 461-469, 1992). For introspective evaluation concerning sleep onset, a sleep onset sensation evaluation scale (Yukari Yamamoto, Hideki Tanaka, Masao Yamazaki, and Shuichiro Shirakawa: Development of a sleep onset sensation questionnaire and analysis of factors influencing sleep onset, Japanese Psychological Research, Vol. 74, pp. 140-147, 2003) was used.

In regard to the scores of the five factors of the MA version of the OSA sleep questionnaire, serving as the main part of the evaluation of the contents of sleep, and in regard to the psychological evaluation upon arising and sleep onset sensation evaluation, the scores of the respective factors, obtained at the time of arising from the fourth day to the sixth day under the conditions of the test tablets of Example 1 and under the conditions of the control tablets of Comparative Example 1, were averaged for the respective conditions and these average values were used as the scores of the respective conditions of the respective examples. In regard to the objective sleep index measured by actigraphy, the total sleep time during the main night sleep period, the sleep efficiency from sleep onset to arising during the main sleep period, the sleeping times mixed in the 8:00 to 17:59 period and in the 18:00 to 21:59 period, the sleeping time during the night period of 22:00 to 7:59, the activity amounts per minute in the 8:00 to 17:59 period and the 18:00 to 21:59 period, the activity amounts during the night sleep period of 22:00 to 7:59, the intermingled awakening time during the main sleep period, and the intermingled awakening time occurring in the first half and latter half of the sleep period as determined by halving the main period were tabulated. The respective averages of the third night to the fifth night under the respective conditions were calculated as the values for the respective examples and conditions.

For statistical examination, a non-parametric test according to the Wilcoxon matched-pairs signed-rank test was carried out for the conditions of both the test tablets of Example 1 and the control tablets of the Comparative Example 1. Since humans are the subjects in the present tests, it was judged that, when the statistical difference with respect to the control tablets of Comparative Example 1 is such that p<0.10, though the result is not significant as an effect, it is adequate as an improvement effect.

Subjects of Analysis

Among the 13 test subjects who were day-working males, one subject worsened extremely in the introspective sleep in the first and second nights of administration of the test tablets of Example 1, and this example of extreme worsening of the introspective sleep at the initial stage of administration of the test tablets of Example 1 gradually improved to recovery thereafter. As a result of examining the personality characteristics obtained in the screening of this example, it was judged that the above was not due to a direct effect of administration of the test tablets of Example 1. Since this example was judged to have worsened in sleep state to a problematic level due to causes other than the administration of the test tablets of Example 1, this example was excluded from being subject to analysis. The final day-working male subjects were thus 12 males of age 25 to 36 (28.0±1.0). Of the 13 male university student test subjects, 2 subjects violated the protocol of the "lifestyle during the research cooperation period" and were thus eliminated from being subject to analysis and the experiment was interrupted for 1 subject who complained of a stomachache due to a cold during the period of administration of the test tablets of Example 1. The final male university student subjects were thus 10 healthy male university students of age 20 to 33 (27.0±1.5). In regard to the effects of the test tablets of Example 1 on the introspective sleep and psychological state at the time of arising, the 22 abovementioned day-working males and male university students (age: 27.5±0.9) were subject to analysis.

Figure 2:
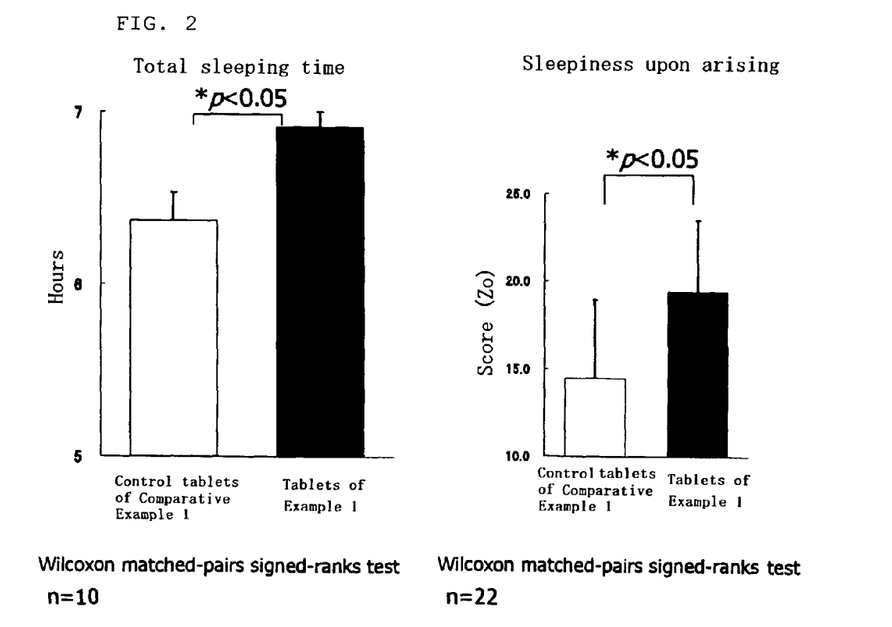
[FIG. 2] Graphs of evaluations concerning total sleeping time and sleeping time extension of sleeping time.

Effects of the Test Tablets of Example 1 on Introspective Sleep by the MA Version of the OSA Sleep Questionnaire at the Time of Arising Evaluation of the results concerning the first factor of sleepiness upon arising, the second factor of sleep initiation and sleep maintenance, and the third factor of dream quality indicated that the tablets of Example 1 exhibited a significant improvement (p<0.05) in regard to sleepiness upon arising over the control tablets of Comparative Example 1 (FIG. 2, right side). Significant differences were not seen in regard to sleep initiation and sleep maintenance and dream quality.

Analysis of the results concerning the fourth factor of recovery from fatigue and the fifth factor of elongation of sleep length indicated no significant differences in regard to these factors between the tablets of Example 1 and the control tablets of Comparative Example 1.

Effects of Theanine/Chamomile on Subjective Sleep Indices Measured by Actigraphy Based on the method of Cole and others, wake and sleep were judged in the continuous records of the activity amounts of 10 male university students. The start of sleep that continued for no less than 10 minutes from 22:00 onwards was deemed to be the sleep onset, and the start of continuous, stable awakening for no less than 10 minutes prior to 10:00 the next morning was deemed to be the arising. The period from sleep onset to arising was deemed to be the main sleep period, and the cumulative sleeping time in this period was deemed to be the sleeping time. The sleep efficiency was calculated as (sleeping time/duration of main sleep period)×100. The results of the sleeping time measured by actigraphy were analyzed. The sleeping time during the main sleep period was approximately 6 hours and 20 minutes for the control group, approximately 6 hours and 53 minutes for the tablets of Example 1, and a significant difference (p<0.05) was seen (FIG. 2, left side). A significant difference was not seen in terms of the sleep efficiency. The subjects of the present experiment were young males of young adulthood who are originally good in sleep efficiency and exhibited a good sleep efficiency of little less than 94% even under the conditions of the control tablets of Comparative Example 1.

Effects of Examples 1 to 12

In the same manner as in the Test Example 1 and Test Example 2, comparison of the effects with respect to the control tablets were conducted for the respective test tablets of Examples 1 to 11 and the combined use of theanine and cedrol of Example 12.

The effects shown in Tables 4 and 5 below were thus obtained.

TABLE 4

| | Sleepiness upon arising (score (Z(c)) | |
|---|---|---|
| Example No. | Test group (average ± SEM) | Control group (average ± SEM) |
| 1 | 18.11 ± 1.6 | 14.1 ± 2.6 |
| 2 | 16.8 ± 3.2 | |
| 3 | 18.16 ± 4.6 | |
| 4 | 17.35 ± 2.6 | |
| 5 | 16.6 ± 2.5 | |
| 6 | 19.0 ± 1.3 | |
| 7 | 18.2 ± 1.1 | |
| 8 | 17.4 ± 2.8 | |
| 9 | 16.8 ± 3.1 | |
| 10 | 17.5 ± 2.7 | |
| 11 | 18.0 ± 2.2 | |
| 12 | 17.1 ± 3.1 | |

TABLE 5

| | Sleeping time (Score (Z(c)) | |
|---|---|---|
| Example No. | Test group (average ± SEM) | Control group (average ± SEM) |
| 1 | 6 H 53 M ± 12 M | 6 H 20 M ± 25 M |
| 2 | 7 H 05 M ± 21 M | |
| 3 | 6 H 48 M ± 18 M | |
| 4 | 7 H 18 M ± 22 M | |
| 5 | 6 H 51 M ± 11 M | |
| 6 | 6 H 56 M ± 16 M | |
| 7 | 7 H 03 M ± 13 M | |
| 8 | 6 H 45 M ± 10 M | |
| 9 | 6 H 50 M ± 11 M | |
| 10 | 7 H 07 M ± 19 M | |
| 11 | 6 H 44 M ± 8 M | |
| 12 | 6 H 57 M ± 14 M | |

"H" means hours.
"M" means minutes.

Since in regard to the sensation of elongation of sleep length, sleep initiation and sleep maintenance, dream quality, intermingled awakening, intermingled awakening in the latter half of the main sleep period, significant differences were not seen between the control group and the test group, the data shall be omitted.

Thus in the comparison between the combined uses of theanine and the other components and intake of theanine solitarily, significant differences were confirmed in regard to sleepiness upon arising and extension of the sleeping time. It can thus be understood that in comparison to the case where theanine is administered solitarily, combined use of theanine and the other components can promote better sleep.

Example 13

Production of Theanine/Chamomile Blended Candy

As an example of the sleep improvement composition, a theanine/chamomile blended candy was produced using the raw materials shown in Table 6 below.

TABLE 6

| Material | Weight |
|---|---|
| Granulated sugar | 41 kg |
| Starch syrup | 23 kg |
| Theanine | 10 kg |
| Chamomile | 60 kg |
| Fragrance (lemon flavor) | 0.05 kg |
| 50% tartaric acid | 1 kg |
| Water | 30 kg |

While dissolving the granulated sugar in 20 kg of water, the solution was heated to 110° C. and then the remaining 10 kg of water in which the theanine was dissolved, the chamomile, and the starch syrup were added. The solution temperature was then raised to 145° C. Heating was then stopped and the 50% tartaric acid was added and mixed. Then upon cooling to 75 to 80° C., the solution was molded in a molding roller to prepare the theanine/chamomile blended candy.

Measurement of the content of theanine in the candy showed the content to be 89.6 mg/g in one candy of 1.2 g.

Examples 14 to 23

Besides adding lavender, Saint John's wort, kawakawa, valerian, passion flower, tryptophan, 5-HTP, serotonin, γ-aminobutyric acid, or melatonin by the weight % indicated in Table 7 below in place of chamomile in Example 13, the same operations as those of Example 13 were performed to produce candies (the candies of Examples 13 to 24 shall hereinafter be referred to as "test candies").

TABLE 7

| Example | Chamomile substitute | Added weight (kg) |
|---|---|---|
| 14 | Lavender | 20 |
| 15 | Saint John's wort | 10 |
| 16 | Kawakawa | 4 |
| 17 | Valerian | 20 |
| 18 | Passion flower | 50 |
| 19 | Tryptophan | 10 |
| 20 | 5-HTP | 10 |
| 21 | Serotonin | 10 |
| 22 | γ-aminobutyric acid | 10 |
| 23 | Melatonin | 10 |

Example 24

With cedrol, which is a volatile component, a combined-used test was conducted in which cedrol of an amount calculated to provide a cedrol concentration in air of approximately 1 μg/L was taken along with theanine-containing candy prepared by omitting chamomile from the candy of Example 13.

Example 25

Production of Theanine/Chamomile Blended Blueberry Drink

As an example of the sleep improvement composition, a theanine/chamomile blended drink was produced using the raw materials shown in Table 8 below.

TABLE 8

| Material | Weight |
|---|---|
| Fructose and glucose | 12 kg |
| Blueberry juice concentrate | 1 kg |
| 1/5 transparent lemon juice | 0.4 kg |
| Sodium citrate | 0.05 kg |
| 50% sodium citrate (crystals) | For pH adjustment |
| Theanine | 0.1 kg |
| Chamomile | 0.6 kg |
| Fragrance (blueberry flavor) | 0.05 kg |
| Water | Suitable amount |
| Total amount | 100 kg |

The fructose/glucose, blueberry juice concentrate, 1/5 transparent lemon juice, sodium citrate, chamomile and theanine were added to water and dissolved by stirring. The pH was then adjusted to 3.1 using 50% sodium citrate (crystals), and after raising the temperature to 95° C., the fragrance was added and the mixture was filled into 100 ml containers and cooled to produce the theanine/chamomile blended blueberry drink. As a result of determining the quantity of theanine in the blueberry juice, the content was found to be 98.3 mg/100 ml.

Examples 26 to 35

Besides adding lavender, Saint John's wort, kawakawa, valerian, passion flower, tryptophan, 5-HTP, serotonin, γ-aminobutyric acid, or melatonin by the weight % indicated in Table 9 below in place of chamomile in Example 25, the same operations as those of Example 25 were performed to produce drinks (the drinks of Examples 25 to 35 shall hereinafter be referred to as "test drinks").

TABLE 9

| Example | Chamomile substitute | Added weight (kg) |
|---|---|---|
| 26 | Lavender | 0.2 |
| 27 | Saint John's wort | 0.1 |
| 28 | Kawakawa | 0.04 |
| 29 | Valerian | 0.2 |
| 30 | Passion flower | 0.5 |
| 31 | Tryptophan | 0.1 |
| 32 | 5-HTP | 0.1 |
| 33 | Serotonin | 0.1 |
| 34 | γ-aminobutyric acid | 0.1 |
| 35 | Melatonin | 0.1 |

Example 36

With cedrol, which is a volatile component, a combined-used test was conducted in which cedrol of an amount calculated to provide a cedrol concentration in air of approximately 1 μg/L was taken along with a theanine-containing drink prepared by omitting chamomile from the drink of Example 25.

Example 37

Production of Theanine/Chamomile Blended Grapefruit Drink

As an example of the sleep improvement composition, a theanine/chamomile blended drink was produced using the raw materials shown in Table 10 below.

TABLE 10

| Material | Weight |
|---|---|
| Fructose/glucose solution | 6 kg |
| Theanine | 0.1 kg |
| Chamomile | 0.6 kg |
| Ferric pyrrolate | 0.06 kg |
| Placenta extract | 0.01 kg |
| 100% grapefruit juice | 30 kg |
| Sodium citrate | For pH adjustment |
| Fragrance (grapefruit flavor) | 0.05 kg |
| Water | Suitable amount |
| Total amount | 100 kg |

The fructose/glucose solution, theanine, chamomile, ferric pyrrolate, placenta extract and 100% grapefruit juice were added to water and dissolved by stirring. The pH was then adjusted to 3.1 using sodium citrate, and after raising the temperature to 95° C., the fragrance was added and the mixture was filled into containers of 100 ml each and cooled to produce the theanine/chamomile blended grapefruit drink. As a result of determining the quantity of theanine in the grapefruit juice, the content was found to be 96.4 mg/100 ml.

Examples 38 to 47

Besides adding lavender, Saint John's wort, kawakawa, valerian, passion flower, tryptophan, 5-HTP, serotonin, γ-aminobutyric acid, or melatonin by the weight % indicated in Table 11 below in place of chamomile in Example 37, the same operations as those of Example 37 were performed to produce drinks (the drinks of Examples 37 to 47 shall hereinafter be referred to as "test drinks").

TABLE 11

| Example | Chamomile substitute | Added weight (kg) |
|---|---|---|
| 38 | Lavender | 0.2 |
| 39 | Saint John's wort | 0.1 |
| 40 | Kawakawa | 0.04 |
| 41 | Valerian | 0.2 |
| 42 | Passion flower | 0.5 |
| 43 | Tryptophan | 0.1 |
| 44 | 5-HTP | 0.1 |
| 45 | Serotonin | 0.1 |
| 46 | γ-aminobutyric acid | 0.1 |
| 47 | Melatonin | 0.1 |

Example 48

With cedrol, which is a volatile component, a combined-used test was conducted in which cedrol of an amount calculated to provide a cedrol concentration in air of approximately 1pg/L was taken along with a theanine-containing drink prepared by omitting chamomile from the drink of Example 37.

Intake prior to sleep of the test candies of Examples 13 to 24, the test drinks of Examples 25 to 36, and the test drinks of Examples 37 to 48 exhibited the same effects as those of Examples 1 to 12 in regard to alleviation of fatigue upon arising, sensation of elongation of sleep length, sleep initiation and sleep maintenance, dream quality, sleeping time, intermingled awakening (across the entirety of the main sleep period), intermingled awakening in the latter half of the main sleep period, and sleep efficiency in general. That is, it was found that in regard to the improvement of sleep disorders, combined use of theanine and the other components improves on the sleepiness upon arising and elongates the sleeping time and thus promotes better sleep in comparison to the use of theanine solitarily.

Thus by the present embodiments, sleep improvement compositions are provided with which one, who is dissatisfied with sleep, is made to feel as if having slept for a long time upon arising, is made to feel that the fatigue sensation is eliminated and feel a high feeling of refreshment upon arising, is enabled to sleep soundly without sleep disturbances due to nightmares and frequent dreaming, is improved in sleep efficiency due to reduce of intermingled awakening during sleep, and is improved in terms of intermingled awakening especially in the latter half of sleep in the morning hours. These compositions can be applied to the development of various foods, drinks, and medical drugs.

What is claimed is:

1. A method of improving sleep behavior of a subject, the method comprising (i) advance testing the subject by Mosley personality inventory, CMI health examination, and sleep health questionnaire, the subject having no illness that is being treated wherein the sleep behavior is (1) sleepiness upon rising that is evaluated by using the middle-aged version of the Obstructive Sleep Apnea sleep questionnaire, and (2) extending sleeping time that is evaluated by using an actigraph, and then (ii) orally administering to the subject a composition comprising: (a) theanine; and (b) at least one component selected from the group consisting of chamomile, Saint John's wort, kawakawa, passion flower, tryptophan, and γ-aminobutyric acid in amounts effective to improve conditions (1) and (2) above.

2. The method of claim 1, wherein the composition is included in food ingested by the subject.

3. The method of claim 1, wherein the composition is included in a drug ingested by the subject.

4. The method of claim 1, wherein component (b) is passion flower.

* * * * *